United States Patent [19]

Ewing et al.

[11] Patent Number: 5,020,525

[45] Date of Patent: Jun. 4, 1991

[54] ANKLE DISTRACTION APPARATUS

[75] Inventors: John Ewing, Akron; Dan Olson, Dover, both of Ohio; Walter P. Preston, Statesville, N.C.

[73] Assignee: Zimmer, Inc., Warsaw, Ind.

[21] Appl. No.: 409,074

[22] Filed: Sep. 19, 1989

[51] Int. Cl.$^5$ .................................................. A61F 5/04
[52] U.S. Cl. .................................... 128/84 R; 128/75; 128/71
[58] Field of Search ................ 128/69, 70, 71, 72, 128/73, 74, 75, 84 R, 84 A, 84 B, 84 C, 83, 85

[56] References Cited

U.S. PATENT DOCUMENTS

| | | |
|---|---|---|
| 1,188,711 | 6/1916 | Wilting . |
| 1,239,789 | 9/1917 | Hawley . |
| 1,380,297 | 5/1921 | Hughes ............................ 128/84 C |
| 1,576,781 | 4/1924 | Philips . |
| 1,837,037 | 2/1927 | Gillberg . |
| 1,853,693 | 2/1928 | Masland . |
| 1,950,948 | 11/1929 | Murray . |
| 2,034,680 | 2/1933 | Longfellow . |
| 2,865,367 | 12/1958 | Sorenson ............................ 128/71 |
| 3,086,519 | 7/1960 | Pari . |
| 3,680,551 | 8/1972 | Bell et al. ........................ 128/84 R |
| 4,114,611 | 9/1978 | Lyle et al. . |
| 4,181,125 | 1/1980 | Carlson et al. ..................... 128/84 C |

OTHER PUBLICATIONS

Guhl, James F., Arthroscopy: The Journal of Arthroscopic and Related Surgery 4(3):160-167, New Concepts (Distraction) in Ankle Arthroscopy, vol. 4, No. 3 (1988).

Yates, Carlan K., et al., Arthroscopy: The Journal of Arthroscopic and Related Surgery 4(2):101-105, "A Simple Distraction Technique for Ankle Arthroscopy", vol, 4, No. 2 (1988).

*Primary Examiner*—Richard J. Apley
*Assistant Examiner*—Lynne A. Reichard
*Attorney, Agent, or Firm*—Sherman and Shalloway

[57] ABSTRACT

An apparatus is disclosed which provides distraction of the talo-tibial joint so as to allow performance of arthroscopic surgery of the ankle. The apparatus is readily connectable to a standard operating table and allows for adjustment of the amount of tension induced to the patient's ankle. The apparatus includes a unique foot engaging device which includes only two straps; a first calcaneus strap and a second dorsum strap. The straps are connected to one another and to the foot and ankle of the patient by use of hook and loop-type material fasteners. The use of such fastening material allows ready adjustment of the straps about the patient's foot and ankle so as to provide proper plantar and dorsiflexion when the cable of the distraction apparatus is attached to the ends of the calcaneus strap.

11 Claims, 2 Drawing Sheets

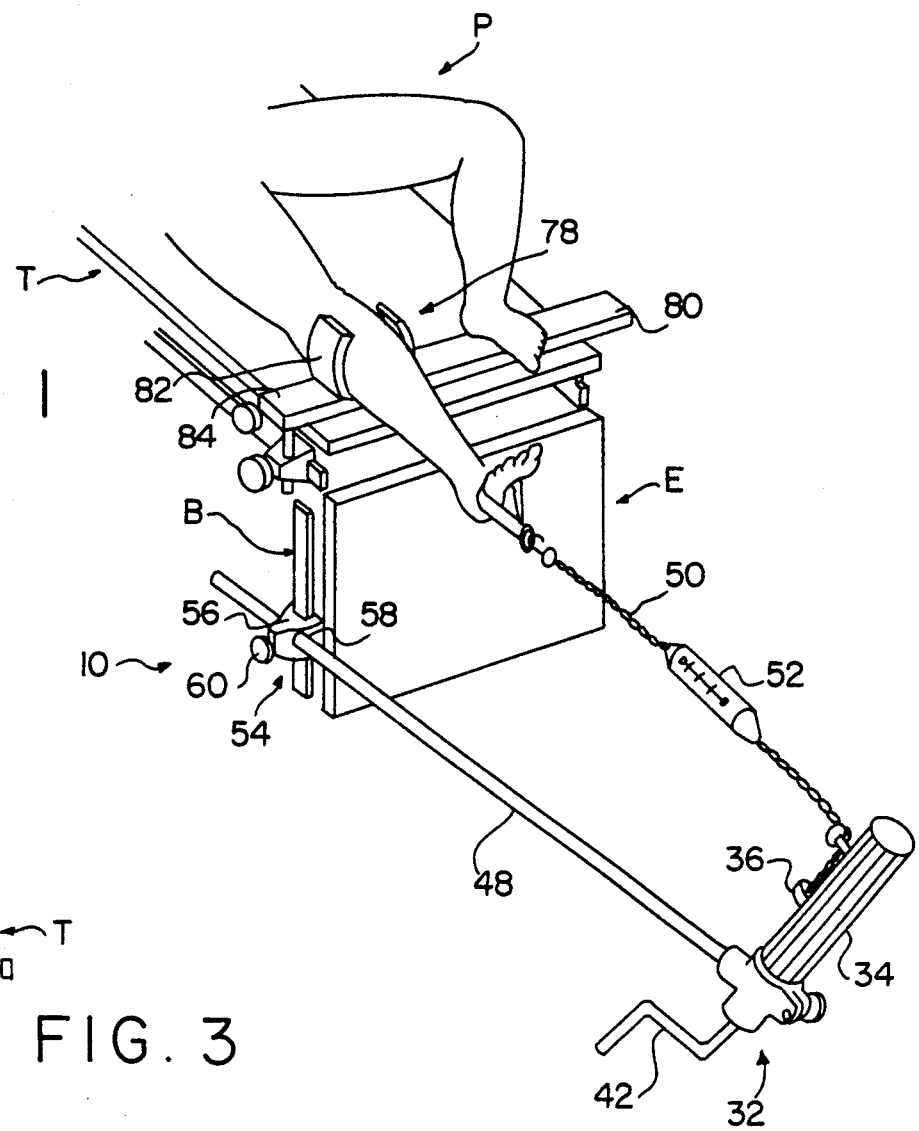
FIG. 1
FIG. 3
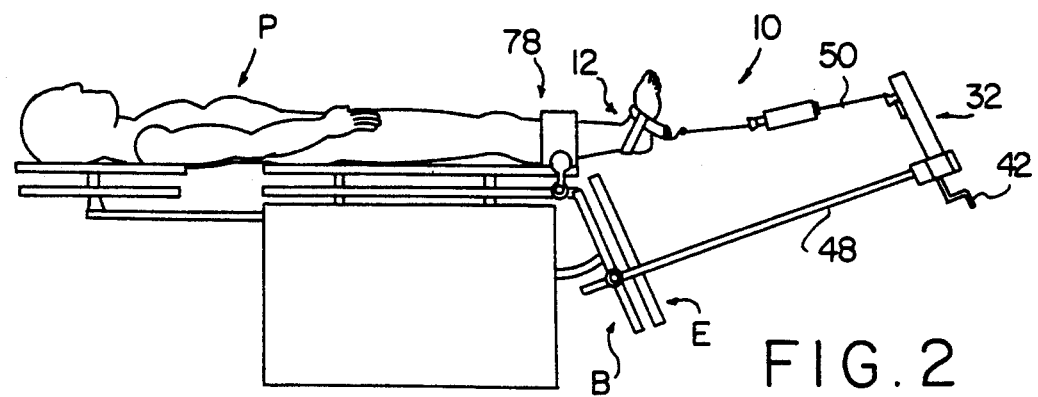
FIG. 2

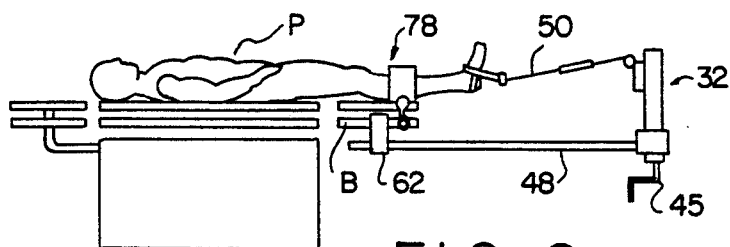
FIG. 8
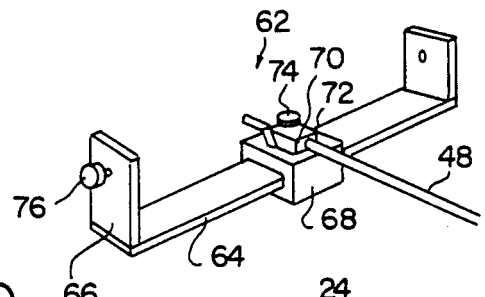
FIG. 9
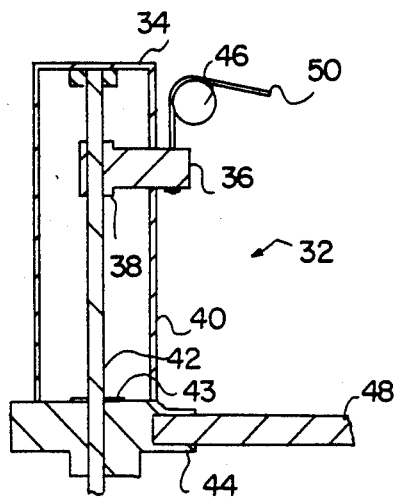
FIG. 7
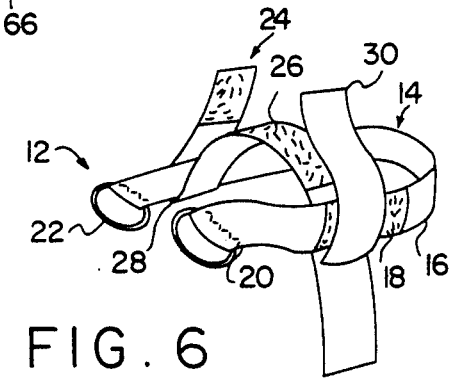
FIG. 6
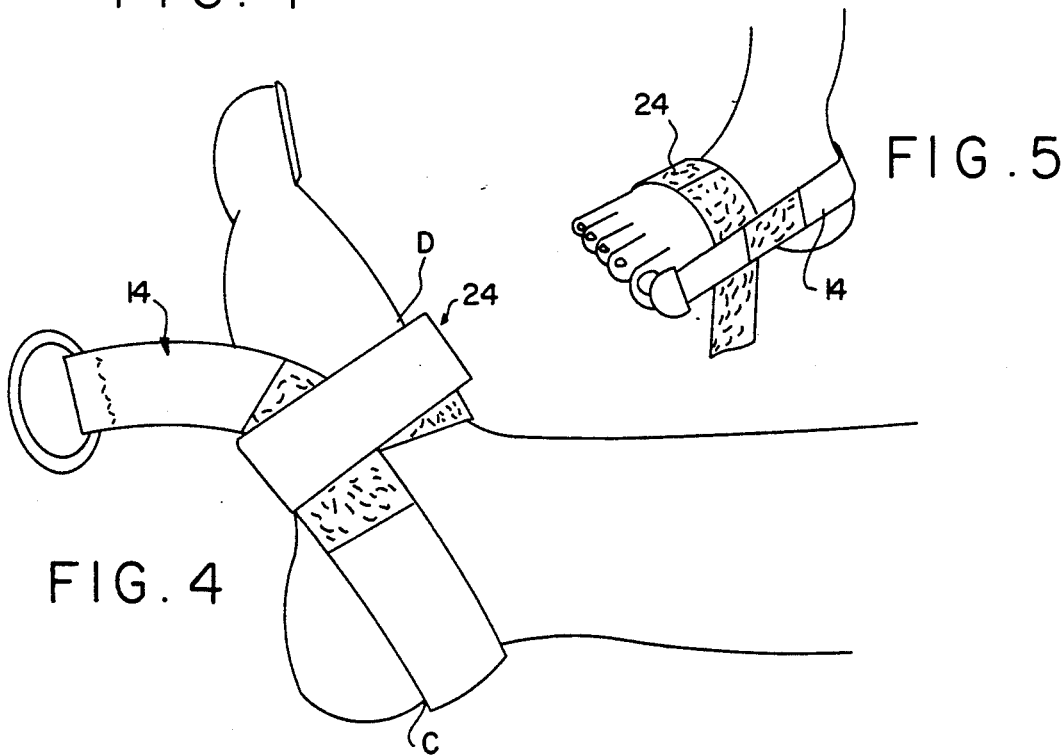
FIG. 5
FIG. 4

ANKLE DISTRACTION APPARATUS

BACKGROUND OF THE INVENTION

1. Field Of The Invention

The present invention is directed generally to an apparatus for use in performance of ankle arthroscopy and more particularly to an apparatus used to provide distraction of the talo-tibial joint during performance of arthroscopic surgery of the ankle.

2. Description Of The Prior Art

Providing traction to various portions of a patient's body is a well established method of providing therapy to overburdened muscles, tendons and ligaments. Over the years, numerous devices have been proposed for providing various types and degrees of traction to different body parts. For example, U.S. Pat. No. 1,837,037 to Gillberg discloses a rather complicated device used to provide therapeutic traction to a patient suffering from excessive contraction of the muscles, ligaments and tendons. The device is a self-supporting unit used in connection with an operating table or hospital cot and provides traction to arms, legs or other body parts by way of suitable harnesses.

U.S. Pat. No. 3,086,519 to Pari provides a very simple device used to provide traction for a patient in a standard type bed. The device is contemplated for use at home to provide traction without requiring alteration of a standard bed.

A self-contained, portable traction device is described in U.S. Pat. No. 4,114,611 to Lyle et al. and is contemplated for use in the home, office or hospital. The device includes a longitudinally elongated frame within which the patient is situated. The frame is biased outwardly by spring within its structure, such that tension is applied across various body parts when the patient is connected within the frame by way of suitable harnesses.

U.S. Pat. No. 2,034,680 to Longfellow discloses a device used to provide therapeutic traction to an injured leg. The device includes a self-supporting frame which is used in conjunction with a bed and is constructed such that the patient is able to use a bedpan without disturbing the positioning of his leg.

In U.S. Pat. No. 1,950,948 to Murray, a device is disclosed which is used in the performance of a therapeutic technique known as circumductory manipulation. The device comprises a table structure which includes apparatus for the performance of the circumductory manipulation of various body parts, as well as for applying tension to the body parts so as to tend to elongate the tissues which are being treated.

It is also well known that it is often useful to provide traction to body parts in order to manipulate and set fractures. Various apparatus for the inducement of traction have been proposed for this purpose. For example, U.S. Pat. No. 1,239,789 to Hawley discloses a device used as a foot and leg support connection to an orthopedic table during operation on fractured bones. It allows the operator to manipulate positioning of the foot and leg, while maintaining the affected bones in constant relative positions.

Similarly, U.S. Pat. No. 1,188,711 to Wilting discloses an apparatus for attachment to an orthopedic table and utilized during the setting of fractured bones. It provides tension to the leg so as to allow the surgeon to more easily manipulate the bones. The device includes means to adjust the tension applied to the legs or other body parts and downwardly extending legs to support the device.

In U.S. Pat. No. 1,576,781 to Philips, an apparatus is proposed which is utilized to induce traction to fractured bones so as to reduce deformities and malpositioning of fragments. It is also useful in positioning the body parts during X-rays and the like.

U.S. Pat. No. 1,853,693 to Masland discloses a surgical stirrup appliance for the ankle which is adjustably disposed about the foot and ankle in a proper angular relationship. The device may be attached to a tensioning apparatus for use in inducing traction to a fractured limb so as to aid in fracture reduction.

While the above-described devices are each useful in certain circumstances and for certain purposes, none of them contemplate nor provide for the application of tension to the foot and ankle in order to distract the talo-tibial joint so as to allow for the performance of ankle arthroscopy. The foot and ankle harnesses disclosed in these patents fail to provide the proper positioning and tensioning necessary for the distraction required in the performance of arthroscopic surgery on the ankle. Furthermore, the structures disclosed for providing tension are either very complicated, disadvantageously arranged such that they interfere with and limit the positioning of the surgeon during the operation, or simply inadequate for providing the necessary distraction.

Two articles relating to ankle arthroscopy have been published in *Arthroscopy: The Journal of Arthroscopic and Related Surgery*. A first of these articles "New Concepts (Distraction) in Ankle Arthroscopy" by James F. Guhl, M.D., describes a technique and apparatus for use in distraction of the ankle. The distractor apparatus utilizes placement anchor pins embedded into the bone on longitudinally opposite sides of the talo-tibial joint and a helical screw/nut arrangement which, upon operation, produces outward force against each of the anchor pins. This apparatus will allow the surgeon to produce distraction in the joint but has the disadvantage that it is intrusive, as well as that the apparatus is necessarily arranged across and in proximity to the joint such that it interferes physically with performance of the arthroscopy. A second article "A Simple Distraction Technique for Ankle Arthroscopy" by Carlan K. Yates, M.D. and William A. Grana, M.D., describes a nonintrusive method and apparatus for use in performing ankle arthroscopy. The method utilizes an ankle engaging device formed from Kerlix gauze dressing wrapped and tied about the ankle and foot in a particular manner shown in FIGS. 1-4. The Kerlix gauze is situated such that it wraps around the calcaneous of the foot and over the dorsum of the foot and provides a downwardly extending loop end which is dropped to the floor, such that the surgeon's or assistant's foot can be placed therein in order to provide downward traction and thus distraction of the joint. With this foot engaging device formed by the Kerlix gauze, the amount of plantar and dorsiflexion can be adjusted by the movement of various loops of the tied gauze material. This arrangement, while an improvement over the intrusive method of the first mentioned article, is disadvantageous in that the wrapping and tying of the various loops of the gauze is cumbersome in that the adjustments to the amount of flexion are made with difficulty and possible inaccuracy due to the nature of the wrappings. Furthermore, the fact that the surgeon or assistant must place his foot in the downwardly extending loop and provide distraction thereto causes either the surgeon or assistant to be less mobile in his efforts to perform the surgery and further does not allow for a constant and readily adjustable tension upon the distracted joint.

SUMMARY OF THE INVENTION

It is thus an object of the present invention to overcome the disadvantages and difficulties encountered in the prior art devices.

It is also an object of the present invention to provide a distraction apparatus for use in ankle arthroscopy.

A further object of the present invention is to provide a distraction apparatus which is easily set up and which interferes as little as possible with maneuverability of the surgeon during surgery.

A still further object of the present invention is to provide a means for engaging the ankle in providing ankle distraction which is readily applied to the foot and provides reliable, accurate and adjustable positioning of the ankle during distraction and arthroscopic surgery.

Yet another object of the present invention is to provide a distraction apparatus for ankle arthroscopy which is readily adjustable in various directions and amounts of tension.

A further object of the present invention is to provide a distraction apparatus for use in the performance of ankle arthroscopy which is relatively inexpensive and readily mountable to an operating table.

Further objects and advantages will become apparent to those of ordinary skill in the art in connection with the following description of the invention.

The present invention comprises a distraction apparatus which provides non-invasive talo-tibial distraction for use in the performance of arthroscopic surgery of the ankle. The apparatus is designed to be clamped to a standard operating table and extend forwardly therefrom in an approximately longitudinally direction. The device includes an ankle engaging device adapted to be disposed about the patient's ankle, a tension producing device for providing adjustable tension to the ankle engaging device in a direction away from the patient's body and along a line substantially longitudinal of the patient's leg, a support bar extending outwardly from the operating table and supporting the tension producing device, and a clamp device which is attached to one or both sides of the operating table and clamps the support rod so that the support rod is longitudinally adjustable. The ankle engaging device includes a first calcaneus strap which is wrapped about the calcaneus portion of the patient's foot and extends forwardly therefrom, and a second dorsum strap which is draped over the dorsal portion of the foot and extends downwardly therefrom. Each of the calcaneus and dorsum straps includes hook and loop fastener material, e.g., VELCRO®, attached thereto. The dorsum strap, in use, is disposed beneath the calcaneus strap and has free ends which are wrapped upwardly about the calcaneus strap such that the free ends come in contact with an upper portion of the dorsum strap and are connected thereto above the dorsum of the foot by the hook and loop fastener material At each free end of the forward end of the calcaneus strap, there is disposed a ring which is used for attachment with the tension producing device.

The tension producing device includes a cable which is attached to the rings of the calcaneus strap at its first end and attached to an adjustable tensioner device at its other end. The adjustable tensioner device includes a housing which is fixed to the support rod, and a movable part which is adjustably mounted to the housing and movable with respect to the house upon operation of a hand crank. A tensionometer is disposed between portions of the cable so as to detect and display the amount of tension induced to the patient's ankle.

BRIEF DESCRIPTION OF THE DRAWING FIGURES

The ankle distraction apparatus of the present invention will now be more fully described in connection with the accompanying drawing figures in which:

FIG. 1 is a perspective view of a first embodiment of the present invention in its operative position connected to an operating table;

FIG. 2 is a side elevation view of the embodiment shown in FIG. 1;

FIG. 3 is an end elevation view of the embodiment shown in FIG. 1;

FIG. 4 is a side view of the ankle engaging device of the present invention in its operative position on a patient's ankle;

FIG. 5 is a perspective view of the ankle engaging device shown in FIG. 4;

FIG. 6 is a more detailed perspective view of the ankle engaging device;

FIG. 7 is a vertical cross section view of the adjustable tensioner of the present invention;

FIG. 8 is a side elevation view of a second embodiment of the present invention; and FIG. 9 is a perspective view of a clamping device used in the second embodiment of the present invention.

DETAILED DESCRIPTION OF THE INVENTION

A first embodiment of the ankle distraction apparatus of the present invention is shown in FIGS. 1–3 in which the apparatus is shown attached to a standard operatigg table T on which a patient P is lying. As usual, the operating table includes a downwardly adjustably folding foot extension E. The foot extension, as well as the remaining portions of the operating table, has side bars B connected thereto disposed beneath the support surface longitudinally along sides of the table. The distraction apparatus 10 is connected to the side bars B of the foot extension E.

The ankle distraction apparatus 10 includes an ankle engagement device 12 which is operatively disposed about the patient's foot and ankle when his leg is extended forwardly and horizontally. A cable 50 is connected at one end to the ankle engagement device 12 and at the other end to a tension adjustment device 32 which provides for the inducement of adjustable amounts of tension to the patient's ankle by way of the ankle engagement device 12 and the cable 50. A tensionometer 52 is disposed between two portions of the cable 50 so as to detect and display the amount of tension induced in the cable and thus induced to the patient's ankle. The tension adjustment device 32 is fixedly attached to one end of an elongated support bar 48. A second end of the elongated support bar 48 is connected in a clamp device 54 which in this embodiment is a standard Clark attachment and is connected to one of the side bars B of the downwardly folding foot extension E.

Although not always necessary, it may be convenient in certain circumstances to provide a leg positioning device 78 on the forward end of the operating table. This leg positioning device includes a transverse support member 80 connected to the operating table by any suitable means such as standard Clark attachments and upright elements 82, preferably formed to conform with the patient's leg, which are mounted in a T-shaped slot 84 extending along the length of the transverse support member 80. The upright elements 82 are slidably disposed in the T-shaped slot 84 such that the patient's leg may be moved transversely into the most advantageous position. Although in the preferred embodiment, the uprights are mounted in a T-shaped slot 84. Any suitable means for mounting the uprights 82 in a transversely slidable manner may be used.

The ankle engagement device 12 will now be described in detail with reference to FIGS. 4-6. The ankle engagement device 12 includes only two straps; a first calcaneus strap and a second dorsum strap. The calcaneus strap 14 includes two free ends 20 with connecting rings 22 attached thereto by way of, for example, the free ends being folded back over and sewn to themselves, thereby capturing the connecting rings 22 in loops formed thereby. The calcaneus strap 14 also includes a center portion 16 which is wrapped about the achilles tendon proximal to its attachment to the os calcis. Intermediate the center portion 16 and the free ends 20 of the calcaneus strap are engagement portions 18 each which include on an outer side thereof a first portion of a hook-and-loop type material such as VELCRO. The second dorsum strap 24 includes a center part 26 which is draped over the dorsum of the foot such that its free end parts 30 extend downwardly therefrom. Between these free end parts 30 and the center part 26 are intermediate parts 28 which are located so as to engage with the engagement portions 18 of the calcaneus strap. Each of the center part 26, the intermediate parts 28 and the end parts 30, include hook-and-loop type fastening material such as VELCRO on the upper surface thereof. The hook-and-loop type material disposed on the intermediate parts is of the opposite complimentary portion of the hook-and-loop type material to that disposed on the engagement portions of the calcaneus strap 14. The hook-and-loop type material disposed on the central part 26 of the dorsum strap 24 is of a complimentary portion of the material to that disposed on the free end parts 30 of the dorsum strap This provides that the free end parts 30 of the dorsum strap can be folded back over the calcaneus strap 14 so as to engage with the center part 26 of the dorsum strap. The calcaneus strap 14 is thus disposed within and through the loop formed by this fold-back feature of the dorsum strap 24. The mutually complimentary hook-and-loop type material portions on the intermediate part of the dorsum strap and the engagement portions of the calcaneus strap, respectively, make a firm connection so as to firmly engage the foot and ankle of the patient. As is apparent, this arrangement utilizing the hook-and-loop type material allows for readily made adjustments to the fit and positioning of the ankle engagement device 10 about the foot and ankle of the patient. Various adjustments may be made in order to vary the amount of plantar and dorsiflexion of the foot and ankle during the period when tension is placed on the ankle by the distraction apparatus 10. Because such adjustments are made so easily, the engagement device 12 may be arranged on the foot and ankle in the most advantageous position.

The tension adjustment device 32 will now be described with reference to FIG. 7. As discussed previously, the device is fixedly attached to the elongated support bar 48. In this regard, an opening is formed in the base 44 of the adjustment device and the bar 48 is disposed therein. The bar 48 may be clamped within the opening in any suitable manner such as by use of a set screw or bolt. A housing 34 is disposed on and extends upwardly from the base member 44. A longitudinal slot 40 is formed along one side of the housing member 34 through which is disposed a moveable member 36. This movable member 36 includes a nut portion 38 which includes internal helical threads complimentary to external threads of a crank member 42 which extends therethrough. The crank member includes a lower bent crank end 45 which is rotated by hand so as to cause vertical translation of the movable member 36 within slot 40 of housing 34. The crank member 42 may be maintained within the housing by any suitable means, but it is contemplated that the crank member 42 will include a radially outwardly extending lower flange 43 to maintain its vertical position within the housing. The inclusion of various bearings and washers to aid in rotation of the crank will be apparent to those skilled in the art. An idler pulley 46 is mounted rotatably to the outside upper portion of the housing 34 and the cable 50 trained thereover. The free end of the cable is connected to a movable member 36 in any suitable manner such as through a hole therethrough with a knot or other stop means disposed at the free end of the cable, or about a rod or other engagement means disposed at an upper surface of the movable member 36. It will thus be apparent that upon rotation of the downwardly extending crank arm 45 of the crank member 42, the complimentary helical threads of the crank member 42 and the nut 38 of the movable member 36, respectively, will cause the vertical translation of the movable member 36 within slot 40 of housing 34; and thus will increase or lessen the tension imparted within cable 50 and thus imparted to the ankle of the patient.

In the first embodiment, the ankle distraction apparatus 10 is mounted to a side bar B of the downwardly folding adjustable foot extension E of the operating table T. In this regard, a Clark attachment 54 is slidably disposed along the side bar B and includes an opening 58 therethrough through which the elongated support bar 48 is disposed The opening 58 is formed in the clamp block 56 which also includes therein a set screw 60 which is utilized to clamp down onto the elongated support bar 48 and thus maintain it in a desired longitudinal position.

In a second embodiment shown in FIGS. 8 and 9, the ankle distraction apparatus 10 of the present invention includes an alternative clamping device 62 for clamping the elongated support bar 48 to the operating table T. This clamping device 62 includes a transverse fastening member 64 and two upright end members 66 which extend upwardly from each end of the transverse fastening member 64. These upright end members 66 are positioned so as to attach about the outsides of each of the opposite side bars B of the foot extension E of the operating table T. The transverse fastening member 64 and the upright end members 66 are attached to the side bars by way of set screws 76 through each of the upright end members 66. A clamp block 68 is slidably disposed about the transverse fastening member 64 and includes thereon a clamp block grip element 70. An opening 72 is disposed longitudinally through the clamp block grip element 70 through which elongated support bar 48 is disposed A set screw 74 is provided through the clamp block grip element 70 so as to secure the elongated support bar 48 in a longitudinal position within the grip element 70.

In operation of the first embodiment shown in FIGS. 1-3, the patient is placed in an upwardly facing horizontal position on the operating table T with the leg to be operated on extending forwardly over the nd of the table. The elongated bar 48 of the distraction apparatus 10 is locked in the Clark attachment 54 such that the elongated bar 48 is at an angle of approximately 50° to 60° to the horizontal. The foot extension E of the operating table T is then adjusted downwardly from its horizontal position by about 50° such that the traction cable will be in approximate alignment with the longitudinal axis of the patient's leg. The ankle engagement device 12 is placed onto the patient's ankle and foot in an advantageous position for the particular situation at hand, and the cable 50 is attached to the connecting rings 22 of the ankle engagement device. The second end of the cable is connected to the movable member 36 of the tension adjustment device 32, such that rotation of the crank member 42 which causes vertical translation of the movable member 36 will cause an increase or decrease in tension induced to the patient's ankle and more particularly to the talo-tibial joint of the patient. The amount of tension of course will determine the amount of distraction of the joint; it has been found that 20 to 30 pounds of tension is generally proper for ankle arthroscopy. The amount of tension induced in the cable 50 is readily determined by viewing the tensionometer 52 which is of any known type.

If a leg positioning device 78 is to be used, the leg is placed between the two uprights 82 and the uprights are positioned at the transverse location which is most advantageous to the particular situation. Other adjustments which may be made to conform the apparatus to the particular situation include longitudinal and vertical adjustment of the elongated support bar 48, additional or lessened tension of the cable 50, and a greater or lesser angle which the elongated support bar 48 makes with the horizontal. Furthermore, a very important adjustment may be made by adjusting the relative positioning of the calcaneus and dorsum straps of the ankle engaging device 12. Such adjustment will allow greater or lesser plantar and dorsiflexion so as to provide the proper distraction of the ankle. The manner in which the patient's leg extends over the front portion of the operating table advantageously provides ready access to the ankle, such that the surgeon and assistants may perform posterior approaches to the ankle when desired.

The operation of the second embodiment of the present invention as shown in FIGS. 8 and 9 is similar to that of the first embodiment, with the exception that the elongated bar 48 is clamped to the foot extension E, rather than to the main portion of the operating table T, by way of clamp device 62. Because the foot extension remains in its horizontal position, the patient is positioned forwardly further than in the first embodiment, such that his leg will be extended forwardly of the operating table. If the leg positioning device 78 is used, it will be clamped to the forward end of the foot extension. This embodiment has the advantage that, being connected on both sides of the table, it is inherently more stable, but has the disadvantage that its angular relationship with respect to the extension of the patient's leg is not adjustable.

Various changes and modifications may be made to the preferred embodiments disclosed without departing from the spirit and scope of the present invention. Thus it is to be understood that the invention is to be limited in scope only by the appended claims.

What we claim is:

1. An ankle distraction apparatus for use in performing ankle arthroscopy on a patient situated on an operating table, comprising:

ankle engaging means for engaging a patient's ankle;
   tension means, operably connectable to said ankle engaging means, for providing adjustable tension to said ankle engaging means in a direction away from a patient's body and along a line substantially longitudinal of a patient's leg;
   support means for supporting said tension means in a position spaced from said operating table; and
   clamp means for clamping said support means to said operating table;
   said ankle engaging means comprising a first strap and a second strap;
   said first strap, operably connectable to said tension means, including a central portion for wrapping about an achilles tendon proximal to its attachment to the os calcis and two attachment portions situated on opposite sides of said central portion and spaced apart therefrom;
   said second strap including a central part having a bottom surface for wrapping contact with the dorsum of a patient's foot and a top surface, intermediate parts located outwardly of said central part and having upper surfaces with means thereon for releasable attachment to respective ones of said attachment portions of said first strap, and two end parts located outwardly of respective ones of said intermediate parts and having upper surfaces with means thereon for releasable attachment to said top surface of said central part.

2. An ankle distraction apparatus as recited in claim 1, wherein said two attachment portions of said first strap include thereon first portions of hook-and-loop type connectors, and said means for attachment on the upper surface of said intermediate parts of said second straps comprise second portions of hook-and-loop type connectors which are connectable with said first portions.

3. An ankle distraction apparatus as recited in claim 2, wherein said top surface of said central part of said second strap includes thereon a first portion of a hook-and-loop type connector, and said means for attachment on the upper surfaces of said two end parts of said second strap comprise second portions of a hook-and-loop type connector.

4. An ankle distraction apparatus as recited in claim 1, wherein said tension means includes tension adjustment means, operably connectable to said support means, for adjusting the amount of tension induced to a patient's talo-tibial joint through said ankle engaging means, and means for connecting said tension adjustment means to said ankle engaging means, said means for connecting said tension adjustment means to said ankle engaging means comprising a connector and a tension detecting means, said connector having a first end connectable to said ankle engaging means and a second end connectable to said tension detecting means, said tension detecting means operably connected to said tension adjustment means.

5. An ankle distraction apparatus as recited in claim 4, wherein said first strap further comprises two free ends, each of said free ends associated with a respective attachment portion, each of said free ends disposed on the opposite side of said respective attachment portion from said central portion, each of said free ends having connector means thereon for connection with said connector.

6. An ankle distraction apparatus as recited in claim 4, wherein said support means comprises an elongated bar and said clamp means comprises a clamp which is attached to a side of a downwardly adjustably foldable foot extension of said operating table and has an opening therethrough through which said elongated bar is longitudinally adjustably disposed, such that adjustment of said foot extension causes adjustment of said elongated bar, of said tension means and thus of the angle at which tension is applied to said patient's talo-tibial joint.

7. An ankle distraction apparatus as recited in claim 4, wherein said support means comprises an elongated bar; and said clamp means comprises a transversely elongated fastening member with uprights at each end thereof for attachment on opposite sides of said operating table, and a clamp block transversely slidably attached to said fastening member, said clamp block including a means for longitudinally adjustably gripping said elongated bar.

8. An ankle engaging device for use in providing distraction of a patient's talo-tibial joint, comprising:
- a first strap, operably connectable with a tension applying device, including a central portion for wrapping about an achilles tendon proximal to its attachment to the os calcis and two attachment portions situated on opposite sides of said central portion and spaced apart therefrom; and
- a second strap including a central part having a bottom surface for wrapping contact with the dorsum of a patient's foot and a top surface, intermediate parts located outwardly of said central part and having upper surfaces with means thereon for releasable attachment to respective ones of said attachment portions of said first strap, and two end parts located outwardly of respective ones of said intermediate parts and having upper surfaces with means thereon for releasable attachment to said top surface of said central part.

9. An ankle engaging device as recited in claim 8, wherein said two attachment portions of said first strap include thereon first portions of hook-and-loop type connectors, and said means for attachment on the upper surfaces of said intermediate parts of said second straps comprise second portions of hook-and-loop type connectors which are connectable with said first portions.

10. An ankle engaging device as recited in claim 9, wherein said top surface of said central part of said second strap includes thereon a first portion of a hook-and-loop type connector, and said means for attachment on the upper surfaces of said two end parts of said second strap comprise second portions of a hook-and-loop type connector.

11. An ankle engaging device as recited in claim 9, wherein said first strap further comprises two free ends, each of said free ends associated with a respective attachment portion, each of said free ends disposed on the opposite side of said respective attachment portion from said central portion, each of said free ends having connector means thereon for connection with a tension applying device.

* * * * *